United States Patent [19]

Absil et al.

[11] Patent Number: 5,173,461
[45] Date of Patent: Dec. 22, 1992

[54] TOLUENE DISPROPORTIONATION CATALYST

[75] Inventors: Robert P. Absil, West Deptford; Scott Han, Lawrenceville; David S. Shihabi, Pennington; David O. Marler, Deptford; Clarence D. Chang, Princeton; Donna M. Mitko, Monmouth Junction, all of N.J.

[73] Assignee: Mobil Oil Corporation, Fairfax, Va.

[21] Appl. No.: 497,046

[22] Filed: Mar. 21, 1990

[51] Int. Cl.$^5$ .............................................. B01J 29/28
[52] U.S. Cl. ....................................... 502/62; 502/71; 502/77
[58] Field of Search ............................. 502/62, 71, 77

[56] References Cited

U.S. PATENT DOCUMENTS

| | | | |
|---|---|---|---|
| 3,525,775 | 8/1970 | Bolton et al. | 502/62 |
| 4,117,026 | 9/1978 | Haag et al. | 260/671 R |
| 4,117,028 | 9/1978 | Hahn | 260/825 |
| 4,145,315 | 3/1979 | Rodewald | 502/71 |
| 4,231,899 | 11/1980 | Chen et al. | 502/62 |
| 4,296,083 | 10/1981 | Rollmann | 502/62 |
| 4,469,806 | 9/1984 | Forbus et al. | 502/62 |
| 4,477,583 | 10/1984 | Rodewald | 502/62 |
| 4,851,604 | 7/1989 | Absil et al. | 585/475 |
| 4,885,426 | 12/1989 | Chu et al. | 585/474 |

OTHER PUBLICATIONS 248 (1984), D. H. Olson et al., "Structure Selectivity Relationship in Xylene Isomerization and Selective Toluene Disproportionation", Catalytic Materials Relationship Between Structure and Reactivity.

Primary Examiner—Carl F. Dees
Attorney, Agent, or Firm—Alexander J. McKillop; Charles J. Speciale; Marina V. Schneller

[57] ABSTRACT

A catalyst comprising a molecular sieve having a lattice aluminum content in which the silica/alumina framework mole ratio is less than 55, and having a diffusion rate constant of less than about 150 sec$^{-1} \times 10^{-6}$ is particularly useful for vapor-phase disproportionation of toluene.

24 Claims, 1 Drawing Sheet

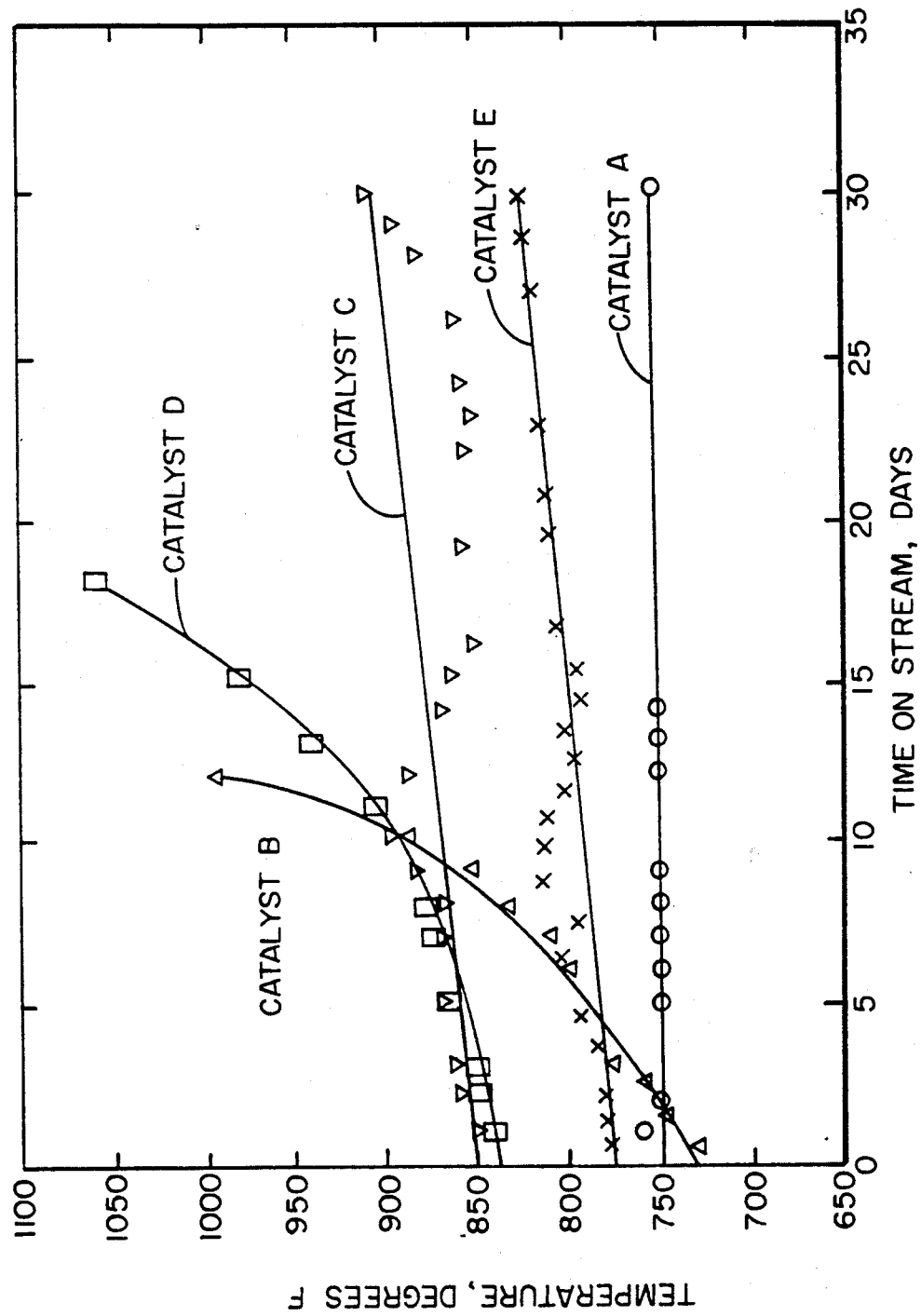

TOLUENE DISPROPORTIONATION CATALYST

FIELD OF THE INVENTION

The invention is a molecular sieve containing catalyst. The molecular sieve has a lattice aluminum content with a framework silica/alumina mole ratio of less than 55, a diffusion rate constant $(D/r^2)$ of less than 150 $\sec^{-1} \times 10^{-6}$ and a Constraint Index of from about 1 to about 12. An improved process for vapor-phase disproportionation of toluene is based on the presence of the catalyst which exhibits excellent aging properties at low start of cycle temperatures.

BACKGROUND OF THE INVENTION

Zeolitic materials, both natural and synthetic, have been demonstrated in the past to have catalytic properties for various types of hydrocarbon conversions. Certain zeolitic materials are ordered, porous crystalline molecular sieves having a definite crystalline structure within which there are a large number of smaller cavities which may be interconnected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Prior art techniques have resulted in the formation of a great variety of synthetic molecular sieves. These materials have come to be designated by convenient symbols, as illustrated by ZSM-5 (U.S. Pat. No. 3,702,886).

The use of certain molecular sieves as catalyst components is taught in U.S. Pat. No. 4,305,808, for example.

The silica/alumina molar ratio of a given molecular sieve is often variable; for example, zeolite X (U.S. Pat. No. 2,882,244) can be synthesized with a silica/alumina ratio of from 2 to 3; zeolite Y (U.S. Pat. No. 3,130,007) from 3 to about 6. In some molecular sieves, the upper limit of silica/alumina ratio is virtually unbounded. ZSM-5 is one such material wherein the silica/alumina ratio is at least 5. U.S. Pat. No. 3,941,871 (Re. 29,948) discloses a porous crystalline silicate made from a reaction mixture containing no deliberately added alumina and exhibiting an X-ray diffraction pattern characteristic of ZSM-5. U.S. Pat. Nos. 4,061,724; 4,073,865 and 4,104,294 describe crystalline silicates of varying alumina and metal content.

It is known that zeolites are stabilized for various processes by reducing lattice aluminum content. In FCC applications, for example, the catalyst of choice is ultrastable Y which has been dealuminized from its precursor Y form by steaming. Another example of stability enhancement by catalyst dealuminization is in hydrodewaxing. U.S. Pat. No. 4,247,388 teaches the improvement of catalyst aging characteristics in lube dewaxing by steaming ZSM-5 to reduce lattice aluminum content.

U.S. Pat. No. 4,380,685 teaches para-selective alkylation, transalkylation or disproportionation of a substituted aromatic compound to form a dialkylbenzene compound mixture over catalyst comprising zeolite characterized by a Constraint Index of 1 to 12 and a silica/alumina mole ratio of at least 12/1, the catalyst having thereon incorporated various metals and phosphorus. Other patents covering alkylation and transalkylation include U.S. Pat. Nos. 4,127,616; 4,361,713; 4,365,104; 4,367,359; 4,370,508 and 4,384,155. Toluene is converted to para-xylene in U.S. Pat. Nos. 3,965,207; 3,965,208; 3,965,209; 4,001,346; 4,002,698; 4,067,920; 4,100,215 and 4,152,364, to name a few. Alkylation with olefins is taught, for example, in U.S. Pat. Nos. 3,962,364 and 4,106,218 and toluene is disproportionated in, for example, U.S. Pat. Nos. 4,052,476; 4,007,231; 4,011,276; 4,016,219 and 4,029,716. Isomerization of xylenes is taught in, for example, U.S. Pat. Nos. 4,100,214; 4,101,595; 4,158,676; 4,159,282; 4,351,979; 4,101,597; 4,159,283; 4,152,363; 4,163,028; 4,188,282 and 4,224,141.

U.S. Pat. Nos. 3,551,509 and Re. 27,639 disclose transalkylation between trimethylbenzenes and toluene to yield xylenes and benzene in the presence of a crystalline aluminosilicate catalyst having large pore openings of 8 to 15 Angstrom units and, preferably containing Group VIII metals, hydrogen and rare earth cations.

In the area of aromatic disproportionation, Grandio et al teach in the *Oil and Gas Journal*. Vol. 69, Number 48 (1971) a liquid-phase toluene disproportionation process utilizing zeolite catalysts in the absence of hydrogen. They further teach that vapor-phase toluene disproportionation requires hydrogen recycle or else frequent regeneration of catalyst to keep coke levels low on the catalyst and to maintain catalytic activity over any reasonable period of time.

Otani teaches in *Chemical Engineering*. 77 (16), 118 (1970) that vapor-phase catalytic disproportionation of toluene requires hydrogen recycle to keep the zeolite catalyst from excessive coke build-up and, thereby, maintain reasonable catalyst activity.

U.S. Pat. Nos. 3,126,422; 3,413,374; 3,598,878; 3,598,879 and 3,607,961 show vapor-phase disproportionation of toluene over various catalyst. U.S. Pat. No. 4,117,026, incorporated herein in its entirety by reference, teaches disproportionation over catalyst comprising zeolite having a silica/alumina mole ratio of at least 12, a Constraint Index of 1 to 12 and a specified sorption capacity for xylenes. U.S. Pat. No. 4,117,026 describes coking the catalysts prior to use.

SUMMARY

This invention relates to improved catalytic processes for effecting vapor-phase toluene disproportionation which comprises contacting a toluene charge under conditions effective for accomplishing said vapor-phase disproportionation, including a reactor inlet temperature between about 600° F. and about 1,100° F., a pressure between atmospheric and 1,000 psig, a total feed weight hourly space velocity (WHSV) between about 0.1 $hr^{-1}$ and about 30 $hr^{-1}$ a hydrogen to hydrocarbon mole ratio of from 0 to about 10. The above WHSV is based upon the weight of catalyst molecular sieve, i.e. total weight of active catalyst component.

The catalyst comprises a crystalline molecular sieve having a high lattice aluminum content characterized by a silica/alumina mole ratio of less than 55, preferably from about 20 to about 40, a Constraint Index of from about 1 to about 12 and a diffusion rate constant $(D/r^2)$ of less than about 150 $\sec^{-1} 10^{-6}$, preferably less than about 120 $\sec^{-1} 10^{-6}$.

BRIEF DESCRIPTION OF DRAWING

The drawing is a graph of a plot of temperature (°F.) vs. time on stream.

DETAILED DESCRIPTION

The present invention relates to an improved vapor-phase toluene disproportionation process. U.S. Pat. No. 4,052,476, incorporated herein by reference in its entirety, is illustrative of a prior art vapor-phase process for disproportionation of toluene over a wide range of conditions and with a catalyst composition comprising a crystalline molecular sieve characterized by a silica/alumina mole ratio of at least 12 and a Constraint Index of from 1 to 12, e.g. ZSM-5, ZSM-11, ZSM-12, ZSM-35.

For the present improved process, the catalyst will comprise a crystalline molecular sieve material having a structure which will permit a Constraint Index of from about 1 to about 12 and preferably will comprise a crystal having the structure of ZSM-5, as determined by X-ray diffraction. The silica/alumina framework mole ratio of the molecular sieve for use herein, however, will be less than about 55. The molecular sieve will also display a diffusion rate constant $(D/r^2)$ of less than about 150 $sec^{-1} \times 10^{-6}$. If either the silica/alumina framework ratio or the diffusion rate constant are not as above, the improvement of this invention will not be realized. Preferably, the silica/alumina framework ratio ranges from about 20 to less than about 55, e.g. from about 20 to about 40; and preferably, the diffusion rate constant is less than about 120 $sec^{-1} \times 10^{-6}$ and most, preferably less than 100 $sec^{-1} \times 10^{-6}$.

The catalyst exhibits no, or extremely low, aging rate and high activity at start of cycle temperatures which are lower than can be achieved by catalysts not satisfying those two properties; accordingly, cycle to cycle temperature adjustments are minimal compared to those required by catalysts, not meeting those criteria, because the catalyst retains its activity. The catalyst conversion produces about thermodynamic equilibrium value amounts of p-xylene, generally the most valuable product of toluene disproportionation.

To exceed that thermodynamic equilibrium value of p-xylene during conversion the catalyst can be treated so as to render the catalyst more diffusionally restricted and to reduce reisomerization of the p-xylene formed. The treatment provides a material on the molecular sieve which decreases the diffusion rate constant to below that of the as-synthesized molecular sieve and reduces isomerization and/or reisomerization of p-xylene product.

One such treatment is precoking of the molecular sieve. Typical conditions for precoking include pressures ranging from atmospheric to 600 psig; a weight hourly space velocity (based on the hydrocarbon) of 0.1 to 25; a $H_2$/hydrocarbon ratio of 0 to 5 and a temperature of 900° to 1,200° F. If the zeolite is employed in substantially pure form or in combination with a low coking binder, the amount of coke in the catalyst is less than, when the zeolite is combined with a binder of high coking tendencies, such as alumina; for example, coke content of the total catalyst with an alumina binder can be within the approximate range of 10 to 40 weight percent. Precoking can be accomplished by contacting the catalyst with a hydrocarbon charge, e.g., toluene, under high severity conditions or alternatingly at a reduced hydrogen to hydrocarbon concentration, i.e., 0 to 1 mole ratio of hydrogen to hydrocarbon for a sufficient time to deposit the desired amount of coke thereon.

Alternatively, the catalyst may be treated by combining therewith a small amount, generally in the range of about 2 to about 30 weight percent, of a difficultly reducible oxide, such as an oxide of antimony, phosphorus, boron or magnesium. Combination of the desired oxide with zeolite can readily be effected by contacting the zeolite with a solution of an appropriate compound of the element to be introduced, followed by drying and calcining to convert the compounds to its oxide form.

Alternatively, the molecular sieve catalyst may be surface treated with metallo polymers preferably oxo- and hydroxy-bridge polymers of silica, zirconia, and titania followed by calcination. This modification can be achieved by chemical vapor deposition or impregnation of solutions of the metal polymers. One method of depositing silica on the surface of the molecular sieves can be effected by dissolving a silicone compound, such as those describe below, in a suitable solvent, such as n-hexane, pentane, heptane, benzene, toluene, chloroform, carbon tetrachloride and then contacting the molecular sieve with the resulting solution at a temperature between about 10° C. and about 100° C. for a period of time sufficient to deposit the ultimately desired amount of silicone thereon. Time of contact will generally be within the range of 0.2 to 5 hours, during which time the mixture can be subjected to evaporation. The resulting residue is then calcined in an oxygen-containing atmosphere, preferably air, at a rate of 0.2° to 5° C./minute to a temperature greater than 300° C. but below a temperature at which the crystallinity of the zeolite will be affected. Generally, the temperature will be below 600° C. The product is usually maintained at the calcination temperature for one to twenty-four hours to yield a silica-coated zeolite containing between about 0.5 and about 30 weight percent and preferably between about one and fifteen weight percent silica. Silicone compounds which can be employed in the process to produce silica-coated zeolite include dimethylsilicone, diethylsilicone, phenylmethylsilicone.

The crystalline molecular sieves which can be made to exhibit the above required properties include those having the structure of ZSM-5, ZSM-11, ZSM-5/ZSM-11 intermediate, ZSM-12, ZSM-22, ZSM-23, ZSM-35, ZSM-38, ZSM-48, ZSM-50 and Beta. ZSM-5 is described in U.S. Pat. No. 3,702,886, the contents of which are incorporated herein by reference. ZSM-11 is described in U.S. Pat. No. 3,709,979, the contents of which are incorporated herein by reference. ZSM-5/ZSM-11 intermediate is described in U.S. Pat. No. 4,229,424, the contents of which are incorporated herein by reference. ZSM-12 is described in U.S. Pat. No. 3,832,449, the contents of which are incorporated herein by reference. ZSM-23 is described in U.S. Pat. No. 4,076,842, the contents of which are incorporated herein by reference. ZSM-35 is described in U.S. Pat. No. 4,016,245, the contents of which are incorporated herein by reference. ZSM-38 is described in U.S. Pat. No. 4,046,859, the contents of which are incorporated herein by reference. ZSM-48 is described in U.S. Pat. No. 4,397,827, the contents of which are incorporated herein by reference. ZSM-50 is described in U.S. Pat. No. 4,640,849, the contents of which are incorporated herein by reference. Beta is described in U.S. Pat. No. 3,308,069, the contents of which are incorporated herein by reference.

ZSM-22 is a molecular sieve which can be made to be useful in the present improved process. In general, its as-synthesized composition is as follows:

$$(x)Q_2O:(y)M_{2/n}O:(z)Al_2O_3:100SiO_2$$

wherein $Q_2O$ is the oxide form of an organic compound containing an element of Group VA of the Periodic Table of the Elements, e.g. N or P, preferably N, containing at least one alkyl or aryl group having at least 2 carbon atoms, M is an alkali metal or an alkaline earth metal having a valence n, and $x=0.01-2.0$, $y=0-2.0$ and $z=0-5$.

ZSM-22 has a definite X-ray diffraction pattern, set forth below in Table I, which distinguishes it from other crystalline materials.

TABLE I

| Interplanar d-spacings (A) | Relative Intensity (I/Io) |
|---|---|
| 10.9 ± 0.2 | M-VS |
| 8.7 ± 0.16 | W |
| 6.94 ± 0.10 | W-M |
| 5.40 ± 0.08 | - W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 $I/I_o$ is the intensity of the strongest line or peak, and d (obs.) the interplanar spacing in Angstroms (A), corresponding to the recorded lines, were determined. In Table I, the relative intensities are given in terms of the symbols VS = very strong, M = medium, W = weak, etc. It should be understood that this X-ray diffraction pattern is characteristic of all the species of ZSM-22. Ion exchange of the alkali metal cations with other ions results in substantially the same X-ray diffraction pattern with some minor shifts in interplanar spacing and variation in relative intensity. Other minor variations can occur, depending on the silica/alumina ratio of the particular sample, as well as its degree of thermal treatment.

ZSM-22 can be suitably prepared from a reaction mixture containing a source of silica, an alkane diamine, an alkali metal oxide or an alkaline earth metal oxide (e.g. sodium, potassium, cesium, calcium or strontium), water, and alumina, and having a composition, in terms of mole ratios of oxides, within the following ratios:

| Reactants | Broad | Preferred |
|---|---|---|
| $SiO_2/Al_2O_3 =$ | 20 or more | 30 to 1000 |
| $H_2O/SiO_2 =$ | 10 to 100 | 20 to 60 |
| $OH^-/SiO_2 =$ | 0 to 0.3 | 0.1 to 0.2 |
| $M^+/SiO_2 =$ | 0 to 2.0 | 0.1 to 1.0 |
| $RN/SiO_2 =$ | 0.01 to 2.0 | 0.05 to 1.0 | wherein RN is a $C_2-C_{12}$ alkane diamine of the formula $H_2N-(CH_2)_n-NH_2$ (abbreviated $C_nDN$), $n=2$ to 12, and preferably is 5 to 8, and M is an alkali metal or an alkaline earth metal, and maintaining the mixture at crystallization temperature until crystals of ZSM-22 are formed. Thereafter, the crystals are separated from the liquid by an conventional means, washed and recovered.

The original cations of the above molecular sieves are preferably replaced in accordance with techniques well known in the art, at least in part, with hydrogen or hydrogen precursor cations and/or non-noble metal ions of Group VIII of the Periodic Table, e.g. nickel, iron and/or cobalt.

Diffusivities and diffusion rates herein are determined by measuring the time ($t_{0.3}$) it takes to sorb 30% of o-xylene (of total o-xylene capacity) by the determination described in U.S. Pat. No. 4,117,026, incorporated herein by reference as to that description. The characteristic diffusion time, $t_{0.3}$, is a direct measure of the critical mass transfer property $r^2/D$, where D is the diffusion co-efficient (cm$^2$/sec) and r = the crystal radius (cm) and is determinable by experiment.

Hydrocarbon sorption and diffusion rate measurements have been found to be effective in characterizing and distinguishing between various ZSM-5 preparations. Diffusion parameters are calculated from sorption rates by assuming that the plane sheet model describes the diffusion process in ZSM-5. For every sorbate loading $Q/Q\infty = 0.3$ (for 30% o-xylene of total o-xylene capacity), where $Q\infty$, is the equilibrium sorbate loading, there is a $(Dt/r^2)^{178}$ value where D, t, and r are the diffusion coefficient (cm$^2$/sec), time (sec) [which is determinable by experiment], and crystal radius (cm), respectively. Hence from the sorption time required to reach a given sorbate loading, $D/r^2$ can be calculated directly.

Sorption measurements are carried out with a Dupont Instruments Thermogravimetric Analyzer Model 951 and Sage Instruments Syring Pump Model 355. Xylene sorption and diffusion measurements are made by heating a fresh 50 mg sample of hydrogen form zeolite in flowing nitrogen at 500° C. to a constant weight. The temperature is reduced to 120° C., and either ortho- or para-xylene is delivered to the TGA module by means of the syring pump. The hydrocarbon is instantaneously vaporized and swept over the zeolite by a 60 cc/min nitrogen purge. Para-xylene is used to obtain equilibrium xylene capacity due to the slow equilibrium approach of ortho-xylene.

The members of the class of molecular sieves useful herein have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular molecular sieve solely from theoretical structure considerations.

A convenient measure of the extent to which a crystal provides control to molecules of varying sizes to it internal structure is the Constraint Index of the crystal. Crystalline materials which provide a highly restricted access to and egress from its internal structure have a high value for the Constraint Index, and materials of this kind usually have pores of small size, e.g. less than .5 Angstroms. On the other hand, crystalline materials which provide relatively free access to the internal crystal structure have a low value for the Constraint Index, and usually have pores of large size, e.g. greater than 8 Angstroms. The method by which Constraint Index is determined is described fully in U.S. Pat. No. 4,106,218, incorporated herein by reference for details of the method.

Constraint Index (CI) values for some typical materials are:

| CI (at test temperature) | |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those molecular sieves which are useful in the instant invention. The very nature of this parameter and the recited technique by which it is determined, however, admit of the possibility that a given material can be tested under somewhat different conditions and thereby exhibit different Constraint Indices. Constraint Index seems to vary somewhat with severity of operations (conversion) and the presence or absence of binders. Likewise, other variables, such as crystal size, the presence of occluded contaminants, etc., may affect the Constraint Index. Therefore, it will be appreciated that it may be possible to so select test conditions, e.g. temperature, as to establish more than one value for the Constraint Index of a particular crystalline material. This explains the range of Constraint Indices for some molecular sieves, such as ZSM-5, ZSM-11 and Beta.

It is to be realized that the above CI values typically characterize the specified crystalline materials, but that such are the cumulative result of several variables useful in the determination and calculation thereof. Thus, for a given crystal exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the material, the presence of possibly occluded contaminants and binders intimately combined with the crystal may affect the CI. It will accordingly be understood to those skilled in the art that the CI, as utilized herein, while affording a highly useful means for characterizing the molecular sieves of interest is approximate, taking into consideration the manner of its determination, with the possibility, in some instances, of compounding variable extremes. However, in all instances, at a temperature within the above-specified range of 290° C. to about 538° C., the CI will have a value for any given molecular sieve of interest herein within the approximate range of 1 to 12.

The molecular sieve for use herein or the catalyst comprising same can be thermally treated at high temperatures. This thermal treatment is generally performed by heating at a temperature of at least 370° C. for a least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product is particularly useful in the present process.

For the improved disproportionation process of this invention the suitable molecular sieve may be employed in combination with a support or binder material such as, for example, a porous inorganic oxide support or a clay binder. Non-limiting examples of such binder materials include alumina, zirconia, silica, magnesia, thoria, titania, boria and combinations thereof, generally in the form of dried inorganic oxide gels and gelatinous precipitates. Suitable clay materials include, by way of example, bentonite and kieselguhr. The relative proportion of suitable crystalline molecular sieve of the total composition of catalyst and binder or support may vary widely with the zeolite content ranging from between about 30 to about 90 percent by weight and more usually in the range of about 50 to about 80 percent by weight of the composition. The composition may be in the form of an extrudate, beads or fluidizable microspheres.

Operating conditions employed in the improved process of the present invention are critical. Such conditions as temperature, pressure, space velocity, molar ratio of the reactants and hydrogen to hydrocarbon mole ratio will have important effects on the process.

The improved process of this invention is conducted such that disproportionation of toluene is carried out in the vapor-phase by contact in a reaction zone, such as, for example, a fixed bed of catalyst composition, under disproportionation effective conditions, said catalyst composition being characterized as comprising the above-defined molecular sieve, preferably which has been hydrogen, hydrogen precursor and/or Group VIII metal exchanged and/or thermally treated. The effluent is separated and distilled to remove desired product, such as benzene and xylene, and unreacted reactant, i.e toluene, is recycled for further reaction.

By the present improved process toluene is converted to aromatic concentrates of high value, e.g. xylene and benzene. This process may be conducted in either batch or fluid bed operation with attendant benefits of either operation readily obtainable.

In the process of this invention, the toluene charge is preferably dried in a manner which will minimize the water entering the reaction employed. Means known in the art suitable for drying the toluene charge to the present process are numerous, including percolation through silica gel, activated alumina, molecular sieves or other suitable substance or use of liquid charge dryers.

In a typical embodiment of the present process, optimum toluene conversion is found to be from about 40 weight percent to about 50 weight percent. Yield of $C_5^-$ products and ring losses in such an embodiment appear to increase at conversion above about 40 percent and xylene yields begin to decrease when toluene conversion exceeds about 50 weight percent.

Considering this vapor-phase disproportionation of toluene, the first stage feed is heated to a temperature within the range of about 600° F. to about 1,100° F. at a pressure within the range of about atmospheric to about 1,000 psig. Preferred inlet temperatures for the process of the present invention fall within the range of about 650° F. to about 1,000° F. and preferred pressures fall within the range of about 50 psig to about 1,000 psig. The hydrogen to hydrocarbon mole ratio may be from 0 (no added hydrogen) to about 10, with a preferred range of from 0 to about 3. A particularly preferred range of hydrogen to hydrocarbon mole ratio will be from 0 to about 2.

The following specific examples will serve to illustrate the process of the present invention, without unduly limiting same. In the examples, when Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078 and in *The Journal of Catalysis*, Vol. IV, pp. 522-529 (Aug. 1965), each incorporated herein as to that description. It is noted that instrinsic rate constants for many acid-catalyzed reactions are proportional to the Alpha Value for a particular crystalline silicate catalyst (see "The Active Site of Acidic Aluminosilicate Catalysts," *Nature*, Vol. 309, No. 5959, pp. 589-591, 14 Jun. 1984).

EXAMPLE 1

Five separate molecular sieves were prepared for testing of the present concept and comparisons to determine important process/catalyst limitations.

In order to produce ZSM-5 having the requisite silica:alumina framework mole ratio and diffusion rate constant of the invention the zeolite synthesis gel must have a composition, in mole ratios, of;

| | |
|---|---|
| $SiO_2/Al_2O_3$ | 25 to 100 |
| $H_2O/SiO_2$ | 4 to 25 |
| $OH^-/SiO_2$ | 0.02 to 0.4 |
| $OH^-/H_2O$ | 0.005 to 0.05 | and the crystallization temperature must be at least 250° F. The resulting ZSM-5 will have a silica:alumina framework mole ratio of less than 55 and a diffusion rate constant of from $10\times10^{-6}$ to $100\times10^{-6}$, sec$^{-1}$. Molecular sieve A was produced according to those parameters.

Molecular Sieve A

A 6.4 parts quantity, by weight, of water was mixed with 11.7 parts 50% NaOH, 10.6 parts $Al_2(SO_4)_3$ 14H$_2$O and 71.4 parts amorphous silica (46.5% solids) prepared by the neutralization of sodium silicate with sulfuric acid. The reaction mixture had a composition, in mole ratios of:

| | |
|---|---|
| $SiO_2/Al_2O_3 =$ | 30 |
| $H_2O/SiO_2 =$ | 5.76 |
| $OH^-/SiO_2 =$ | 0.072 |
| $OH^-/H_2O =$ | 0.013 |

The reaction mixture was then heated to 350° F. and stirred in an autoclave at that temperature for crystallization. After full crystallinity was achieved, the resulting crystals were separated from remaining liquid by filtration, washed with water and dried.

Molecular Sieve B

A 7.3 parts quantity, by weight, of water was mixed with 12.8 parts 50% NaOH, 10.1 parts $Al_2(SO_4)_3$ 14 H$_2$O, 1.6 parts ZSM-5 seeds and 68.2 parts amorphous silica (47.6% solids) prepared by the neutralization of sodium silicate with sulfuric acid. The reaction mixture had a composition, in mole ratios, of:

| | |
|---|---|
| $SiO_2/Al_2O_2 =$ | 32 |
| $H_2O/SiO_2 =$ | 5.45 |
| $OH^-/SiO_2 =$ | 0.105 |
| $OH^-/H_2O =$ | 0.0192 |

The reaction mixture was then heated directly to 220° F. and stirred in an autoclave at that temperature for crystallization. After full crystallinity was achieved, the resulting crystals were separated from remaining liquid by filtration, washed with water and dried.

Molecular Sieve C

A 3.1 parts quantity, by weight, of n-propylamine was added to a mixture containing 1.1 parts sodium chloride, 0.2 parts ZSM-5 seeds, 0.2 parts dispersant (mixture of polymerized aryl and substituted benzoid alkyl sulfonic acids), 2.6 parts $Al_2(SO_4)_3$14H$_2$O, 7.0 parts 50% NaOH, 25.8 parts HiSil 233 (a precipitated hydrated $SiO_2$ containing about 6 wt. % free H$_2$O and about 4.5 wt. % bound H$_2$O of hydration and having an ultimate particle size of about 0.02 micron) and 59.9 parts water. The reaction mixture had a composition, in mole ratios, of:

| | |
|---|---|
| $SiO_2/Al_2O_3 =$ | 65 |
| $H_2O/SiO_2 =$ | 9.92 |
| $OH^-/SiO_2 =$ | 0.163 |
| $N/Al_2O_3 =$ | 9.2 |
| $OH^-/H_2O =$ | 0.0165 | wherein N is the n-propylamine. In the above ratios, the hydroxide concentration is based on only inorganic sources.

The reaction mixture was then heated directly to 220° F. and stirred in an autoclave at that temperature for crystallization. After full crystallinity was achieved, the resulting crystals were separated from remaining liquid by filtration, washed with water, exchanged with NH$_4$NO$_3$ and dried.

Molecular Sieve D

A 3.1 parts quantity, by weight, of n-propylamine was added to a mixture containing 1.1 parts sodium chloride, 0.2 parts ZSM-5 seeds, 0.2 parts dispersant (mixture of polymerized aryl and substituted benzoid alkyl sulfonic acids), 2.6 parts $Al_2(SO_4)_3 14\ H_2O$, 7.0 parts 50% NaOH, 25.8 parts HiSil 233 and 59.9 parts water. The reaction mixture had a composition, in mole ratios, of:

| | |
|---|---|
| $SiO_2/Al_2O_3 =$ | 65 |
| $H_2O/SiO_2 =$ | 9.92 |
| $OH^-/SiO_2 =$ | 0.163 |
| $N/Al_2O_3 =$ | 9.2 |
| $OH^-/H_2O =$ | 0.0165 | wherein N is the n-propylamine. In the above ratios, the hydroxide concentration is based on only inorganic sources.

The reaction mixture was then heated directly to 320° F. and stirred in an autoclave at that temperature for crystallization. After full crystallinity was achieved, the resulting crystals were separated from remaining liquid by filtration, washed with water, exchanged with $NH_4NO_3$ and dried.

Molecular Sieve E

A 1.0 parts quantity, by weight, of water was mixed with 7.0 parts 100% NaOH, 10.8 parts $Al_2(SO_4)_3 14\ H_2O$, 75.6 parts amorphous silica (45.2% solids) prepared by the neutralization of sodium silicate with sulfuric acid, and 5.5 parts ZSM-5 seeds (33% solids). The reaction mixture had a composition, in mole ratios, of:

| | |
|---|---|
| $SiO_2/Al_2O_3 =$ | 31 |
| $H_2O/SiO_2 =$ | 4.95 |
| $OH^-/SiO_2 =$ | 0.109 |
| $OH^-/H_2O =$ | 0.0219 |

The reaction mixture was then heated to 220° F. and stirred in an autoclave at that temperature for crystallization. After full crystallinity was achieved, the resulting crystals were separated from remaining liquid by filtration, washed with water and dried.

The above molecular sieve materials were evaluated for diffusion rate constants, composition, e.g. alumina, silica and sodium contents, surface area, particle density, pore volume and Alpha Value. Results of these evaluations are listed in Table II below.

TABLE II

| Molecular Sieve | A | B | C | D | E |
|---|---|---|---|---|---|
| $SiO_2/Al_2O_3$, mole ratio | 26 | 26 | 55 | 55 | 26 |
| Na, ppm | 135 | 120 | 450 | 280 | — |
| Diffusion rate $(D/r^2 \times 10^{-6})$, $sec^{-1}$ | <150 | >150 | >150 | <150 | >150 |
| Surface area, $m^2/g$ | 325 | 317 | 349 | 265 | — |
| Particle density, g/cc | 0.87 | 1.01 | 0.88 | 0.93 | — |
| Pore volume, cc/g | 0.77 | 0.61 | 0.76 | 0.70 | — |
| Alpha Value | 650 | 710 | 350 | 290 | 427 |

EXAMPLE 2

The molecular sieves of Example 1 were each composited with binder alumina and made into extrudates such that Catalyst A comprised 65 wt. % Molecular Sieve A and 35 wt. % alumina, Catalyst B comprised 65 wt. % Molecular Sieve B and 35 wt. % alumina, Catalyst C. comprised 65 wt. % Molecular Sieve C. and 35 wt. % alumina, Catalyst D comprised 65 wt. % Molecular Sieve D and 35 wt. % alumina and Catalyst E comprised 65 wt. % Molecular Sieve E and 35 wt. % alumina.

Each catalyst was then evaluated for toluene disproportionation in identical reactors and at identical reaction conditions. Each catalyst was diluted in the same fashion, 2.3 g Catalyst A with 4.5 g inert sand, 1.1 g Catalysts B,C and D with 1.0 cc inert vycor chips. The reactors were ⅜-inch o.d. stainless steel and the reaction conditions were 600 psig, 4.0 $hr^{-1}$ weight hourly space velocity (based on molecular sieve) and a hydrogen/hydrocarbon mole ratio of 2. Feedstock was dried toluene and a target toluene conversion of 48 ±1 wt. % was maintained. The toluene was dried for each reaction by percolating through activated alumina.

Liquid and gas products from the reactions were analyzed by conventional chromatography. Run data are presented in FIG. 1.

FIG. 1 is a plot of reaction temperature in °F. versus time on stream in days for each of the Example 2 disproportionation runs.

It is noted that for Catalyst A the start-of-cycle temperature was 750° F., which was maintained throughout the run. For Catalyst B, the initial start-of-cycle temperature was 730° F. Since Catalyst B aged rapidly, the temperature was corrected for the target conversion when necessary by using a factor of 3 wt. % toluene conversion/10° F. The same aging correction factor was used for the runs with Catalysts C. and D. For Catalyst C., the start-of-cycle temperature was 849° F.; and for Catalyst D, 847° F. Catalyst E reached the 48% target conversion at 775° F. initially and aged to 802° F.

From the data plotted in FIG. 1, it is observed that Catalyst A showed no appreciable aging (<0.1° F./day) over a 30 day cycle. Catalyst E, with a silica/alumina mole ratio of 26, but a diffusion rate of greater than 150 $sec^{-1} \times 10^{-6}$, aged 0.9° F./day over the 30 day cycle. Catalyst C, with a silica/alumina mole ratio of 55 and a diffusion rate constant of greater than 150 $sec^{-1} \times 10^{-6}$ aged over 50° F. in the same 30 day time period, giving an aging rate of 1° F./day. Catalyst B, with a diffusion rate constant greater than 150 $sec^{-1} \times 10^{-6}$, and Catalyst D, with a silica/alumina mole ratio of 55, both showed severe aging at a rate of 10° F./day.

It will be appreciated that the operating conditions for the reaction in accordance with the process of this invention, as exemplified in the foregoing examples, may be varied within the limits specified so that the process may be conducted in vapor-phase, and that various modifications and alterations may be made in the process without departing from the spirit and scope thereof.

EXAMPLE 3

To 0.6 grams of phenylmethylsilicone (molecular weight 1,686) dissolved in 20 cc of n-hexane was added 2.5 grams of HZSM-5 silica-bound extrudate in which the HZSM-5 had a silica/alumina framework ratio of 26:1. The ZSM-5 used in Examples 3-8 exhibited diffusion rate constant of less than $150 \times sec^{-1} \times 10^{-6}$. This sample contained 35% silica as a binder. The mixture was evaporated at 68° F., the residue was calcined in air at 2 degrees/min to 1,000° F. and then maintained at this temperature for 7 hours to yield silica coated catalyst containing 10 wt % silica.

EXAMPLE 4

To 0.6 grams of phenylmethylsilicone (molecular weight 1,686) dissolved in 20 cc of n-hexane was added 2.5 grams of ZSM-5 alumina-bound extrudate the ZSM-5 having a silica/alumina framework mole ratio of 26:1. This sample contained 35% alumina as a binder. The mixture was evaporated at 68° F., the residue was calcined in air at 2 degrees/min to 1,000° F. and then maintained at this temperature for 7 hours to yield silica coated catalyst containing 10 wt % silica.

EXAMPLE 5

To 1.5 grams of phenylmethylsilicone (molecular weight 1,686) dissolved in 40 cc n-hexane was added 3.1 grams of ZSM-5 alumina-bound extrudate in which the ZSM-5 had an as-synthesized framework silica/alumina ratio of 26:1. This sample contained 35% alumina as a binder. The mixture was evaporated at 68° F., the residue was calcined in air at 2 degrees/min to 1,000° F. and then maintained at this temperature for 7 hours to yield silica coated catalyst containing 20 wt % silica.

EXAMPLE 6

To 0.4 grams dimethylsilicone (molecular weight 4,385) dissolved in 20 cc n-hexane was added 2.5 grams of HZSM-5 silica-bound extrudate in which the ZSM-5 had a silica/alumina framework ratio of 26:1. This sample contained 35% silica as a binder. The mixture was evaporated at 68%F, the residue was calcined in air at 2 degrees/min to 1,000° F. and then maintained at this temperature for 7 hours to yield silica coated catalyst containing 10 wt % silica.

EXAMPLE 7

Toluene disproportionation activity of each catalyst was tested in a micro-unit. In each run, 2 to 2.3 grams of the 1/16" extrudate catalyst were mixed with 4-5 grams of sand. The mixtures were then charged to ⅜" o.d. stainless steel reactors and the runs performed under conditions of ~600 psig, 4-8 WHSV (zeolite), 2H$_2$/HC, and 740°-790° F. The toluene used was purified by percolating it through activated alumina. Liquid and gas products were analyzed by G.C. Results for all silica-bound catalysts are summarized in Table 3. Alumina-bound catalysts results are summarized in Table 4.

EXAMPLE 8

Catalyst of Example 3 underwent regeneration conditions with a minimal loss of activity as seen in Table 5.

From Table 3 and 4, under identical conditions, the silica coated silica-bound catalyst selectively to paraxylene was significantly higher than the silica coated alumina-bound catalyst.

TABLE 3
SELECTIVE TOLUENE DISPROPORTIONATION OVER SILICA-BOUND CATALYSTS

| | Unmodified | | | Modified | | | | | |
| | | | | Example 1 | | | Example 2 | | |
| Catalyst Modification | A None | B None | | Phenylmethyl-silicone | | | Dimethyl-silicone | | |
|---|---|---|---|---|---|---|---|---|---|
| Days on Stream | 1 | 2 | 92 | 1 | 3 | 17 | 2 | 3 | 9 |
| Toluene Conv, wt % | 34.5 | 26.2 | 30.9 | 30.4 | 30 | 29.5 | 27.5 | 33.1 | 28.6 |
| WHSV (zeolite) | 4 | 6 | 8 | 4 | 4 | 7 | 6 | 6 | 6 |
| Temperature, °F. | 739 | 739 | 760 | 739 | 739 | 781 | 808 | 826 | 822 |
| Yields, wt % | | | | | | | | | |
| $C_5^-$ | 1.0 | 0.5 | 0.3 | 1.7 | 1.3 | 0.9 | 0.4 | 1.4 | 0.7 |
| Xylenes | 17.5 | 13.7 | 17.0 | 14.9 | 14.6 | 14.5 | 14.6 | 16.7 | 14.8 |
| $C_9^+$ | 1.4 | 1.0 | 0.7 | 0.4 | 0.5 | 0.5 | 0.8 | 1.2 | 0.9 |
| P-xylene selectivity | 24.9 | 25.1 | 26.4 | 65.6 | 67.9 | 75.5 | 58.0 | 54.1 | 56.9 |

TABLE 4
SELECTIVE TOLUENE DISPORPORTIONATION OVER ALUMINA-BOUND CATALYSTS

| | Unmodified | Modified | | | |
| | | Example 2 Phenylmethyl-silicone | | Example 3 Dimethyl-silicone | |
| Catalyst Modification | A None | 10% Silica | | 20% Silica | |
|---|---|---|---|---|---|
| Days on Stream | 2 | 2 | 15 | 2 | 3 |
| Toluene Conv, wt % | 28.0 | 30.3 | 30.2 | 21.0 | 32.0 |
| WHSV (zeolite) | 4 | 4 | 7 | 4 | 4 |
| Temperature, °F. | 685 | 754 | 795 | 740 | 779 |
| Yields, wt % | | | | | |
| $C_5^-$ | 0.4 | 0.6 | 0.5 | 0.3 | 0.3 |
| Xylenes | 14.9 | 15.6 | 16.1 | 11.2 | 17.2 |
| $C_9^+$ | 0.9 | 1.0 | 1.0 | 0.4 | 0.7 |
| P-xylene selectivity | 24 | 27.6 | 29.1 | 54 | 49 |

TABLE 5
SELECTIVE TOLUENE DISPROPORTIONATION OVER FRESH vs. REGENERATED SILICA-BOUND CATALYSTS

| Catalyst | Fresh | | Regenerated | |
|---|---|---|---|---|
| Days on Stream | 8 | 17 | 8 | 17 |
| Toluene Conv, wt % | 30.0 | 29.5 | 31.0 | 30.4 |
| WHSV (zeolite) | 7 | 7 | 7 | 7 |
| Temperature, °F. | 781 | 781 | 790 | 790 |
| Yields, wt % | | | | |
| $C_5^-$ | 1.3 | 0.9 | 1.3 | 1.5 |
| Xylenes | 14.3 | 14.5 | 14.7 | 15.4 |
| $C_9^+$ | 0.4 | 0.5 | 0.8 | 0.8 |
| P-xylene selectivity | 72.1 | 75.5 | 69.1 | 71.1 |

What is claimed is:

1. A toluene disproportionation catalyst consisting essentially of
    (a) a crystal having the structure of ZSM-5 which in the as-synthesized form has a silica to alumina framework mole ration of less than 55 and a diffusion rate constant $(D/r^2)$ of less than 150 $sec^{-1} \times 10^{-6}$
        wherein the diffusion rate constant is based on the time ($t_{0.3}$) it takes to sorb 30% of ortho-xylene of total orth-xylene capacity of said ZSM-5; and a material thereon which is stable under conditions below and wherein the material is free of activity effective to isomerize p-xylene, whereby the catalyst is effective to produce amounts of p-xylene which exceeds the thermodynamic equilibrium value of p-xylene during toluene disproportionation under conditions including a temperature within the range of 600° to 1,100° F. at a pressure of about atmospheric to about 1,000 psig and hydrogen to hydrocarbon mole ratio of from (0) to about 10, and a weight hourly space velocity based upon weight of active catalyst component, of 0.1 $hr^{-1}$ to 30 $hr^{-1}$;

wherein the material comprises a reagent selected from the group consisting of carbon, coke, zirconia, titania, silica and at least one oxide of an element selected from the group consisting of antimony, phosphorus, boron and magnesium wherein the catalyst exhibits an aging rate under said conditions which is dependent on said silica to alumina framework mole ratio and said diffusion rate constant of said crystal having the structure of ZSM-5.

2. The catalyst of claim 1, wherein the silica to alumina ratio is 20 to 50.

3. The catalyst of claim 1, wherein the silica to alumina ratio is 20 to 40.

4. The catalyst of claim 1, wherein the diffusion rate constant of said crystal having the structure of ZSM-5 is less than 120 $sec^{-1} \times 10^{-6}$.

5. The catalyst of claim 1, wherein the diffusion rate constant of said crystal having the structure of ZSM-5 is less than 100 $sec^{-1} \times 10^{-6}$.

6. A toluene disproportionation catalyst consisting essentially of
   (a) a crystal having the structure of ZSM-5 which in the as-synthesized form has a silica to alumina framework mole ration of less than 55 and a diffusion rate constant $(D/r^2)$ of less than 150 $sec^{-1} \times 10^{-6}$; and
   (b) a material thereon which is inert and stable under the conditions below and wherein the material is free of acid activity effective to isomerize p-xylene, wherein the catalyst is effective to produce amounts of p-xylene which exceeds the thermodynamic equilibrium value of p-xylene during toluene disproportionation under conditions including a temperature within the range of 600° to 1,100° F. at a pressure of about atmospheric to about 1,000 psig and hydrogen to hydrocarbon mole ratio of from (0) to about 10 and wherein the material comprises a reagent selected from the group consisting of carbon, coke, zirconia, titania, silica and at least one oxide of an element selected from the group consisting of antimony, phosphorus, boron and magnesium,
   (c) and a matrix material wherein the matrix material is 10 to 70 weight percent of the catalyst.

7. The catalyst of claim 6, wherein the silica to alumina ratio is 20 to 50.

8. The catalyst of claim 6, wherein the silica to alumina ratio is 20 to 40.

9. The catalyst of claim 6, wherein the diffusion rate constant is less than 120 $sec^{-1} \times 10^{-6}$.

10. The catalyst of claim 6, wherein the diffusion rate constant is less than 100 $sec^{-1} \times 10^{-6}$.

11. An extrudate, tablet or pellet consisting of the catalyst of claim 6.

12. An extrudate, tablet or pellet consisting of the catalyst of claim 7.

13. An extrudate, tablet or pellet consisting of the catalyst of claim 8.

14. An extrudate, tablet or pellet consisting of the catalyst of claim 9.

15. An extrudate, tablet or pellet consisting of the catalyst of claim 10.

16. An extrudate, tablet or pellet consisting of the catalyst of claim 3.

17. An extrudate, tablet or pellet consisting of the catalyst of claim 3.

18. An extrudate, tablet or pellet consisting of the catalyst of claim 3.

19. The catalyst of claim 3, wherein the silica to alumina ratio is about 26.

20. The catalyst of claim 8, wherein the silica to alumina ratio is about 26.

21. The catalyst of claim 6, wherein the matrix is silica.

22. The catalyst of claim 7, wherein the matrix is silica.

23. An extrudate, tablet or pellet consisting of the catalyst of claim 22.

24. An extrudate, tablet or pellet consisting of the catalyst of claim 11.

* * * * *